United States Patent
Berci et al.

(10) Patent No.: US 6,875,169 B2
(45) Date of Patent: *Apr. 5, 2005

(54) CAMERA UNIT WITH A COUPLING FOR A DETACHABLE LIGHT AND IMAGE GUIDE

(75) Inventors: George Berci, Los Angeles, CA (US); Marshal B. Kaplan, Beverly Hills, CA (US); James P. Barry, Charlton, MA (US); David Chatenever, Santa Barbara, CA (US); Klaus M. Irion, Liptingen (DE); Andre Erhardt, Wurmlingen (DE); Jurgen Rudischhauser, Tuttlingen (DE); Daniel Mattsson-Boze, Sacramento, CA (US)

(73) Assignee: Karl Storz GmbH & Co. KG (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/739,670

(22) Filed: Dec. 18, 2003

(65) Prior Publication Data

US 2004/0133073 A1 Jul. 8, 2004

Related U.S. Application Data

(63) Continuation-in-part of application No. 10/285,190, filed on Oct. 31, 2002.

(51) Int. Cl.[7] .................................................. A61B 1/04
(52) U.S. Cl. .................... 600/112; 600/131; 600/132; 600/160
(58) Field of Search ................................. 600/112, 117, 600/118, 130–132, 156, 121, 185, 188, 194, 213, 160

(56) References Cited

U.S. PATENT DOCUMENTS 3,986,854 A 10/1976 Scrivo et al.
4,402,313 A 9/1983 Yabe
4,565,187 A 1/1986 Soloway
4,611,888 A 9/1986 Prenovitz et al.
4,807,594 A 2/1989 Chatenever
4,846,153 A 7/1989 Berci
4,901,142 A 2/1990 Ikuno et al.
5,101,807 A 4/1992 Kawashima
5,125,394 A 6/1992 Chatenever et al.
5,193,135 A 3/1993 Miyagi (Continued)

FOREIGN PATENT DOCUMENTS

| CH | 650342 A5 | 9/1985 |
|----|-----------|--------|
| DE | 4002812 A1 | 8/1990 |
| DE | 3914825 C1 | 9/1990 |
| DE | 4445599 A1 | 9/1995 |
| DE | 29506789 U1 | 10/1995 |
| DE | 19715510 A1 | 10/1998 |
| EP | 0501088 A1 | 12/1991 |

OTHER PUBLICATIONS

New Tech, "Flexiscope Multivision", Schmitt, Maucher & Borjes.

The Role of the Universal Video Intubating System In The Management Of The Difficult Airway, Berci, Chhibber, Kaplan, Van De Wiele and Ward, Jul. 2001.

*Primary Examiner*—Beverly M. Flanagan
(74) *Attorney, Agent, or Firm*—St. Onge Steward Johnston & Reens LLC

(57) ABSTRACT

A coupling device for a light and image guiding system that is keyed to prevent incorrect attachment of light and image guides and an interlock that lockingly engages the light and image guides together in an engaged position, the coupling device attached to a portable camera unit that translates optical signals into an electronic format for display.

27 Claims, 11 Drawing Sheets

U.S. PATENT DOCUMENTS

| | | |
|---|---|---|
| 5,239,983 A | 8/1993 | Katsurada |
| 5,261,392 A | 11/1993 | Wu |
| 5,307,804 A | 5/1994 | Bonnet |
| 5,311,859 A | 5/1994 | Monroe et al. |
| 5,329,936 A | 7/1994 | Lafferty et al. |
| 5,498,230 A | 3/1996 | Adair |
| 5,591,119 A | 1/1997 | Adair |
| 5,667,475 A | 9/1997 | Laser et al. |
| 5,682,199 A | 10/1997 | Lankford |
| 5,751,340 A | 5/1998 | Strobel et al. |
| 5,827,178 A | 10/1998 | Berall |
| 5,879,289 A | 3/1999 | Yarush et al. |
| 6,494,826 B1 * | 12/2002 | Chatenever et al. ........ 600/112 |

* cited by examiner

CAMERA UNIT WITH A COUPLING FOR A DETACHABLE LIGHT AND IMAGE GUIDE

PRIORITY DOCUMENT

The present application is a continuation-in-part of U.S. patent application Ser. No. 10/285,190, filed Oct. 31, 2002.

FIELD OF THE INVENTION

The invention relates to a camera unit having a coupling device for detachably connecting to a light and image guide. More specifically, the camera unit/light and image guide device may be utilized with a video laryngoscope or an endoscope for medical procedures.

BACKGROUND OF THE INVENTION

Video cameras are increasingly being utilized for medical procedures. For instance, video laryngoscopes are being utilized to aide the physician in intubating patients. In addition, endoscopes are also being increasingly utilized by physicians in non-invasive procedures for observing a body cavity.

A number of challenges confront physicians in performing surgical procedures. For instance, one of the foremost obstacles encountered by an anesthesiologist in the intubation process include; the remoteness of the location where the tube is to be positioned, the consequent restriction of view as the tube is inserted, variations and anomalies in the anatomy of the patients, an uncomfortable and unnatural position for the anesthesiologist while holding the instrument, the potential need to change blades during the procedure, and the necessity for rapid intubation.

During the intubation process, it should be noted that when the tube is inserted, the patient is asleep, hyperoxygenated and then paralyzed for the procedure, and therefore not breathing. In addition, the ventilator is not yet in operation. This gives the anesthesiologist only about two minutes in which to intubate the patient, inflate the cuff, and start ventilation. If he is delayed because of unsuccessful attempts, he must stop, apply a ventilation mask to the patient, supply oxygen for a time through the mask, remove the mask, adjust medication if necessary, and then start over again. This delays the operation and extends the patient's time under anesthesia. This extension of time while under anesthesia may have very serious consequences, especially for elderly patients.

So too in surgical procedures in which an endoscope is utilized, the quicker and easier the endoscope is to use, the sooner the physician can complete the procedure and bring the patient out from under anesthesia.

With the advent of endoscopic equipment and small cameras, instrumentation has been improved to the extent that it can enable viewing of internal structures such as: the vocal cords and larynx, or any other anatomical feature to be viewed on a video screen. This greatly increases the ease of, for instance, intubation of the patient or viewing of the area in which the surgical procedure is to take place. However, laryngoscopes and endoscopes may be further improved such that they are easier to use, reducing the time involved in, for instance, changing a camera or light and image attachment.

Video laryngoscopes and endoscopes typically contain a light guiding system, usually in the form of fiber optic cables, in order to bring light to the surgical area. The light guiding system typically extends through a handle of the device and to an end portion to be inserted into the body. With a laryngoscope, the blade typically extends through a guide tube located in the blade so as to position the light guiding system to illuminate the area ahead of the blade. Video laryngoscopes and endoscopes also typically contain an image guiding system, for example in the form of a rigid rod lens system. The image guiding system can also be configured as an ordered, flexible fiber optic bundle. The image guiding system is utilized to transmit reflected light from the surgical area to the camera. With a laryngoscope, the image guiding system is utilized to transmit reflected light from ahead of the blade to a camera. The camera, attached at the proximal end of the device, usually contains a CCD (charge coupled device) sensor, in the form of a light-sensitive chip that converts the optical signals into electrical signals that are conveyed from the image-sensing camera module to a remotely located image processing system.

Typically, the combination light guiding system and image guiding system are permanently attached to the handle of the video laryngoscope or endoscope and are continuous, extending from the distal end of the device, through the handle and to the camera for the image guiding system, and to the light source for the light guiding system. Therefore, the light guiding system and image guiding system extending from the handle of the device for insertion typically comprise flexible coherent fiber optic bundles. However, in the case of a video laryngoscope, when changing blades, the fiber optic bundle must be carefully inserted or withdrawn from the opening of the guide tube at the proximal end of the blade. This may take an unacceptable amount time for the physician to thread the bundle into the tube if the blade must be changed in the middle of the intubation process. In addition, in the case of an endoscope, if the camera unit must be changed in the middle of a procedure, it is undesirable to have to remove the endoscope to do this.

The light and image guiding systems have typically been permanently attached to the handle to ensure the system will reliably transmit the illuminating light and reflected images. To utilize a detachably connectable light and image guiding system, the attachment means would have to rigidly hold the member in place such that the light and image guiding systems did not become misaligned. In addition, the attachment means must be easy and quick to operate, making it possible to perform the coupling procedure with as little close attention as possible, but nevertheless reliably. Provision must therefore be made for the coupling elements to be keyed to each other so that the coupling cannot be incorrectly joined and so that close attention by the operation is not required.

In addition, the flexible bundles may easily be damaged and will wear over time, degrading or rendering the system inoperable. As a visual inspection of the device often will not indicate whether the bundles are damaged, it is conceivable that a physician may obtain a damaged or malfunctioning device not realizing that it is damaged. The time involved with determining that the instrument is malfunctioning, withdrawing it, finding another device, and then proceeding with the procedure may have severe adverse effects upon the patient under anesthesia.

Further, video laryngoscopes and endoscopes, as with most medical equipment, must be sterilized after use. Because the light and image guiding systems are permanently attached to the handle, they are exposed to extremely high temperatures, which also cause wear and/or failure of the flexible bundles. In addition, because the camera unit, and the light and image guiding systems are permanently located in the handle, they must be subjected to the sterilization process with the handle and blades, which means that the handle must be hermetically sealed. This can greatly add to the cost in manufacturing the device.

It is therefore desired to provide an improved attachment device that is easy to use and will facilitate the quick removal and reattachment of a camera unit and a light and image guiding attachment.

It is also desired to provide a highly durable light and image guiding attachment that may readily be removed from and attached to a camera unit.

It is further desired to provide an improved attachment device that will reduce manufacturing costs associated with a combination camera unit and light and image guiding attachment.

It is still further desired to provide an improved attachment device that will reliably connect a camera unit and a light and image guiding attachment, while requiring a minimal amount of attention from the user to attach or detach.

It is yet further desired to provide an improved attachment device for use with a video laryngoscope or an endoscope.

It is still further desired to provide a video laryngoscope according to the forgoing having an interchangeable blade.

SUMMARY OF THE INVENTION

These and other objectives are achieved by providing a camera unit having light and image guiding receptacles at one end and light and image cables connected at the other end. The light and image guiding receptacles are engagable with a coupling element, forming a coupling mechanism, the coupling element having light and image guiding stems that correspond to the light and image guiding receptacles respectively.

In one advantageous application of the present invention, the camera unit and the coupling element are utilized for a video laryngoscope system. The video laryngoscope system includes a laryngoscope handle and an interchangeable blade, where the blade is detachably connectable to the handle. Also provided is a light and image guiding attachment that has the coupling element at one end to engage with the light and image guiding receptacles located in the camera unit. The light and image guiding attachment is also detachably connectable to the handle. The camera unit is detachably engagable with the light and image guiding attachment by means of the coupling mechanism, and is further attachable to the handle.

In another advantageous application of the present invention, the camera unit and the coupling element are utilized for an endoscope system. The endoscope system includes an endoscope and the camera unit. The endoscope is provided with the coupling element at one end to engage with the light and image guiding receptacles located in the camera unit. The camera unit is detachably engagable with the endoscope by means of the coupling mechanism.

Accordingly, the coupling mechanism is provided with a first cylindrical stem of specific diameter and specific length, in whose interior is received a proximal end segment of the light guiding system, and which projects from one coupling end of the light and image guiding attachment in the coupling direction. Further, a second cylindrical stem is provided whose length and diameter are greater than the length and diameter of the first stem, having a proximal end segment of the image guiding system being received in the interior of the second stem, and which projects from one coupling end of the light and image guiding attachment in the coupling direction. The second stem coacts with an interlock system arranged in the camera unit forming a rigid mechanical coupling, the first and second stems extending at a distance next to one another. Complementary receptacles corresponding to the two stems, into which the stems penetrate, are provided in the camera unit. The base of the receptacle into which the second stem penetrates is optically for connection to the camera, and the receptacle in which the shorter first stem is receivable is for connection to a light source.

The mechanical, light-guiding, and image-guiding coupling is accomplished by way of a single simple linear displacement operation, in which specifically the two stems are pushed into the corresponding receptacles of the laryngoscope handle. Because one of the two stems is thicker and longer than the other, incorrect (i.e. reversed) insertion is not possible. Because the thicker stem is also simultaneously the longer one, it is possible, without undue attention, to feel for the correspondingly larger receptacle in the camera unit with this thicker and longer stem, and then to close the coupling with an insertion movement. Incorrect attachment is thus no longer possible, since the thicker and longer stem cannot be attached to the smaller-diameter receptacle for the smaller and shorter stem.

The mechanical interlock or coupling is affected simultaneously with this insertion. Because the larger stem is also the longer stem, and it carries the image guiding system, the image-guiding connection occurs at an axial spacing from the light-guiding connection. This feature has the advantage that any stray light that might emerge from the light connection cannot directly come into contact with the image-guiding connecting point located at an axial distance therefrom. The disadvantages of connecting image and light at the same level, or those, for example, of a coaxial arrangement, are thus eliminated.

Because the coupling mechanism is keyed, the physician can therefore, for example, sense the coupling element and its precise grasped position in the coupling region with one hand, and with the other hand can easily sense the camera unit and its grasped position as well, so that the two elements to be coupled can then be inserted into one another without visual contact. This greatly facilitates handling, especially when, during a procedure such as an intubation, one blade must be quickly exchanged for another thereby requiring that the light and image guiding attachment be removed and re-attached along with the new blade.

An interlock system is displaceable transversely to the coupling direction that can be engaged into a recess on the second stem. This feature has the advantage that in order to close and/or release the coupling, the locking element is displaced transversely to the coupling direction and is engaged into or disengaged from the recess on the second stem. These are all procedures that can be controlled, without visual contact, with the fingers of one hand; the snapping of the locking element into and out of the recess on the stem indicates to the operator whether the coupling is closed or open. If the locking element needs to be pushed into the recess, for example to close the coupling, this can be done by simply inserting the stems into their corresponding receptacles; precise locking can be ascertained by an audible sound that the locking element has been engaged. The locking element may comprise for instance, ball catches, hooks, snap lugs, or the like.

The locking element is acted upon by the force of a spring, and radially projects into the receptacle for the second stem. This is advantageous because, the force of the spring presses the locking element into a defined position, and the coupling may be disengaged by the application of a force opposite the coupling direction, namely withdrawing the stems from their respective receptacles. These are all procedures that can be sensed and controlled with the hand's sense of touch, so that no visual attention or observation is necessary when closing and opening the coupling.

The second stem may have a conical segment at the end that is followed by an undercut. The conical segment constitutes an insertion aid upon insertion of the stem into the receptacle, so that exact insertion is guaranteed with even approximate placement. At the same time, the conical surface can be utilized to displace the locking element radially upon insertion.

In addition, the undercut in the second stem may be configured as an annular groove. This forms a relatively large engagement surface with the locking element, so that the mechanical forces acting on the coupling will be dispersed over the entire area, which contributes to mechanical stability and less wear through use.

In addition, the first and second stems along with the receptacles receiving them each have a window. The windows thereby provide a sealed closure for the light and image guiding systems.

The camera unit is detachably connectable to, depending upon the application, a laryngoscope handle or an endoscope, such that it may be detached when, for instance, the handle or the endoscope is to be sterilized. The camera unit has, at one end, the coupling receptacles for the light and image guiding attachment, and at the other end an illumination cable connected to an illumination source and an image cable extending to a display screen. The illumination cable and the image cable may be either permanently attached to the camera unit or may be detachably connected.

In video laryngoscope applications, the light and image guiding attachment is preferably provided with a stainless steel outer casing, or some other suitable rigid enclosure, for protecting the light and image guides. As the light and image guiding attachment is detachable from the handle, the handle does not have to be hermetically sealed for sterilization. Rather, only the light and image guiding attachment need be subjected to sterilization.

Further, in endoscopic applications, the endoscope having the coupling element is preferably provided of a rigid outer casing for protecting the light and image guides therein. The endoscope may comprise either a flexible, semi-flexible, or rigid shaft.

Accordingly, in one advantageous embodiment of the present invention, a coupling mechanism for a light and image guiding system is provided comprising a camera with a housing having an image guiding receptacle and a light guiding receptacle. The coupling mechanism further comprises a coupling element detachably engagable with the camera along a direction of movement, the coupling element having an image guiding stem, for an image guiding system, that is engagable along the direction of movement with the image guiding receptacle, and a light guiding stem, for a light guiding system, that is engagable along the direction of movement with the light guiding receptacle. The coupling mechanism still further comprises an interlock configured as a locking element that is displaceable transversely to the direction of movement where the camera detachably interlocks with the coupling element when in an engaged position, the locking element comprising a recess.

In another advantageous embodiment of the present invention, a light and image guiding coupling mechanism for a camera is provided comprising, a first image guiding system having a first coupling engagable along a direction of movement with a first coupling of a second image guiding system, the first image guiding system communicating with the second image guiding system when the first coupling is engaged with the second coupling. The coupling mechanism further comprises a first light guiding system having a first coupling engagable along a direction of movement with a first coupling of a second light guiding system, the first light guiding system communicating with the second light guiding system when the first coupling is engaged with the second coupling. The coupling mechanism still further comprises an interlock system configured as a locking element with a recess, the locking element displaceable transversely to the direction of movement, the first image guiding system and the first light guiding system interlocking with the second image guiding system and the second light guiding system respectively when in an engaged position.

In yet another advantageous embodiment of the present invention a video laryngoscope coupling mechanism is provided comprising, a handle, a blade detachably connectable to the handle, and a camera detachably connectable to the handle and having a housing with an image guiding receptacle and a light guiding receptacle. The coupling mechanism further comprises a light and image guiding attachment detachably connectable to the handle and having a coupling element detachably engagable along a direction of movement with the camera. The coupling element is provided with an image guiding stem, for an image guiding system, that is engagable along the direction of movement with the image guiding receptacle, and a light guiding stem, for a light guiding system, that is engagable along the direction of movement with the light guiding receptacle.

In still another advantageous embodiment of the present invention, an endoscope coupling mechanism is provided comprising, a camera having a housing with an image guiding receptacle and a light guiding receptacle, and an endoscope having a coupling element detachably engagable along a direction of movement with the camera. The coupling element is provided with an image guiding stem, for an image guiding system, that is engagable along the direction of movement with the image guiding receptacle, and a light guiding stem, for a light guiding system, that is engagable along the direction of movement with the light guiding receptacle.

In yet another advantageous embodiment of the present invention, an endoscope coupling mechanism is provided comprising, an image guiding stem for an image guiding system, the image guiding stem forming an image guiding coupling for connecting along a direction of movement to a camera. The endoscope coupling mechanism further comprises a light guiding stem for a light guiding system, the light guiding stem forming a light guiding coupling for connecting along the direction of movement to a camera. The endoscope coupling mechanism still further comprises an interlock system configured as a locking element, displaceable transversely to the direction of movement, the camera detachably interlocking with the endoscope when in an engaged position, the locking element further comprising a recess.

It is understood that the features mentioned above and those yet to be explained below can be used not only in the respective combinations indicted, but also in other combinations or by themselves, without leaving the context of the present invention.

DETAILED DESCRIPTION OF THE DRAWINGS

Figure 1:
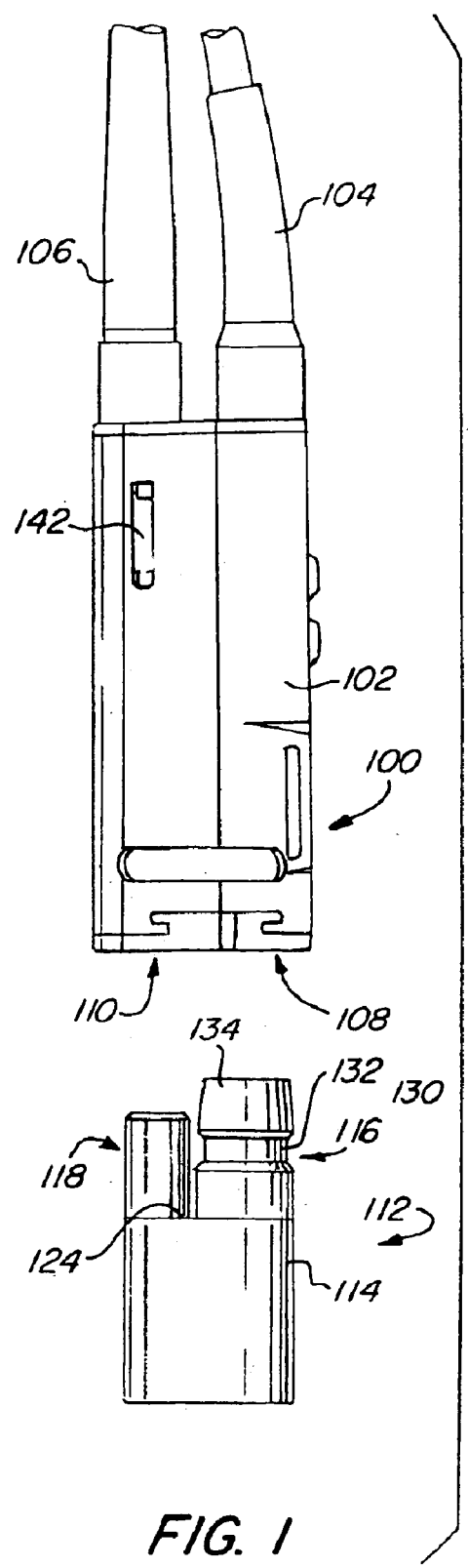
FIG. 1 is an illustration of the camera unit having light and image guiding receptacles at one end and light and image cables connected at the other end, and the coupling element for attachment with the receptacles.

A camera unit 100 according to one advantageous embodiment of the present invention is illustrated in FIG. 1. The camera unit 100, customarily comprising a CCD chip, has a housing 102 that is generally rectangular but may be any shape. At one end, an image guiding cable 104 and light guiding cable 106 are connected to the camera unit 100.

Image guiding cable 104 may comprise an electrical cable, which extends from the camera output (not shown), to a video display (not shown). Image guiding cable 104, may utilize any suitable format and protocol for the transmission of video images. Image guiding cable 104 may be permanently attached to camera unit 100 as illustrated in FIG. 1, or may be detachably connectable to camera unit 100.

Also shown attached to camera unit 100 is light guiding cable 106. Light guiding cable 106 may comprise any suitable cable (typically fiber optic) for the transmission of illuminating light from an illumination source (not shown) to a location to be illuminated. Light guiding cable 106 may comprise coherent or non-coherent fiber optic cables and be permanently attached to camera unit 100 as illustrated in FIG. 1, or may be detachably connectable to camera unit 100. While image guiding cable 104 and light guiding cable 106 are each shown separate from each other, it is contemplated that both may be enclosed in a protective jacket as a single cable.

At the end opposite to where image guiding cable 104 and light guiding cable 106 attach to camera unit 100, image guiding receptacle 108 and light guiding receptacle 110 are provided. These receptacles are more readily seen in FIG. 2 and will be discussed therewith.

It can be seen from FIG. 1 that housing 102 of camera unit 100 is contoured, which allows easy gripping and manipulation of camera unit 100 by a physician even without having to look at the device. Rather, based on the contour of housing 102, a physician will be able to determine by feel, how to position camera unit 100 to connect it with various pieces of equipment. Housing 102 may comprise any rigid material, such as for instance, stainless steel, that will protect the camera unit in a cost effective and durable manner.

Also illustrated in FIG. 1 is coupling element 112. Coupling element 112 comprises coupling element housing 114, along with image guiding stem 116 and light guiding stem 118. The image guiding system extending through light guiding stem 118 comprises a bundle of coherent fiber optic cables to transmit reflected light from an area where illuminated light is be supplied to. Image guiding stem 116 and light guiding stem 118 are shown in further detail in connection with FIG. 3 and will be discussed therewith.

Coupling element housing 114 may comprise any suitable rigid material, such as for instance, stainless steel or a rigid plastic. Coupling element 112 is designed to detachably engage with image guiding receptacle 108 and light guiding receptacle 110.

While coupling element 112 illustrated in FIG. 1 is not specifically shown connected to a particular instrument, it may be used in connection with practically any medical instrument using an illuminating system and an image guiding system. The coupling mechanism is universal and may be easily adapted depending upon the quality and resolution of image desired.

Figure 2:
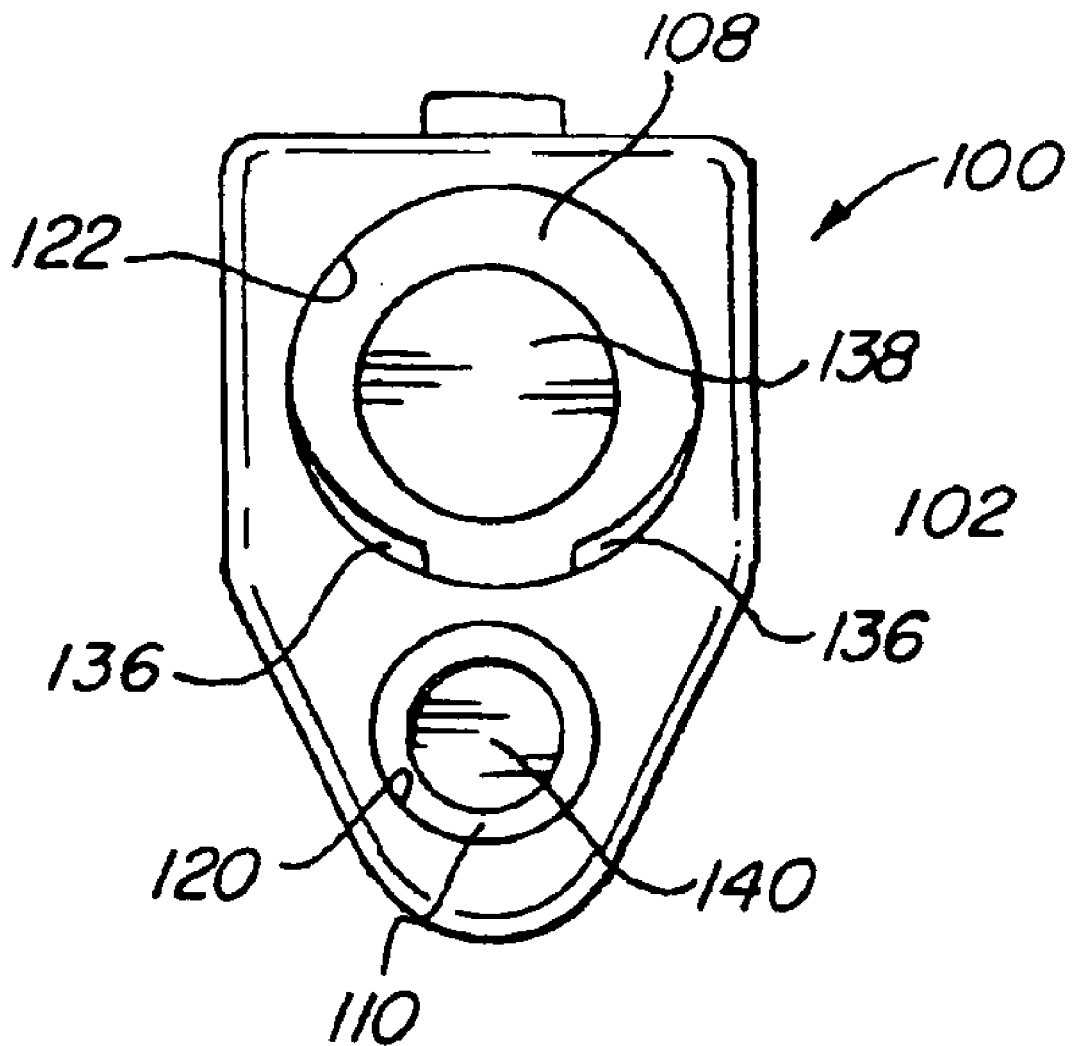
FIG. 2 is a cross-sectional view of the camera unit according to FIG. 1, showing the light and image guiding receptacles.

FIG. 2 is a cross-sectional view of camera unit 100 illustrating image guiding receptacle 108 and light guiding receptacle 110.

The light guiding receptacle 110 and the image guiding receptacle 108 are both contained in housing 102. The light guiding receptacle 110 has an inner surface 120 defining a cross-sectional diameter of the receptacle opening generally corresponding to a diameter of light guiding stem 118. Further, image guiding receptacle 108 has an inner surface 122 defining a cross-sectional diameter of the receptacle opening corresponding to a diameter of image guiding stem 116.

Figure 3:
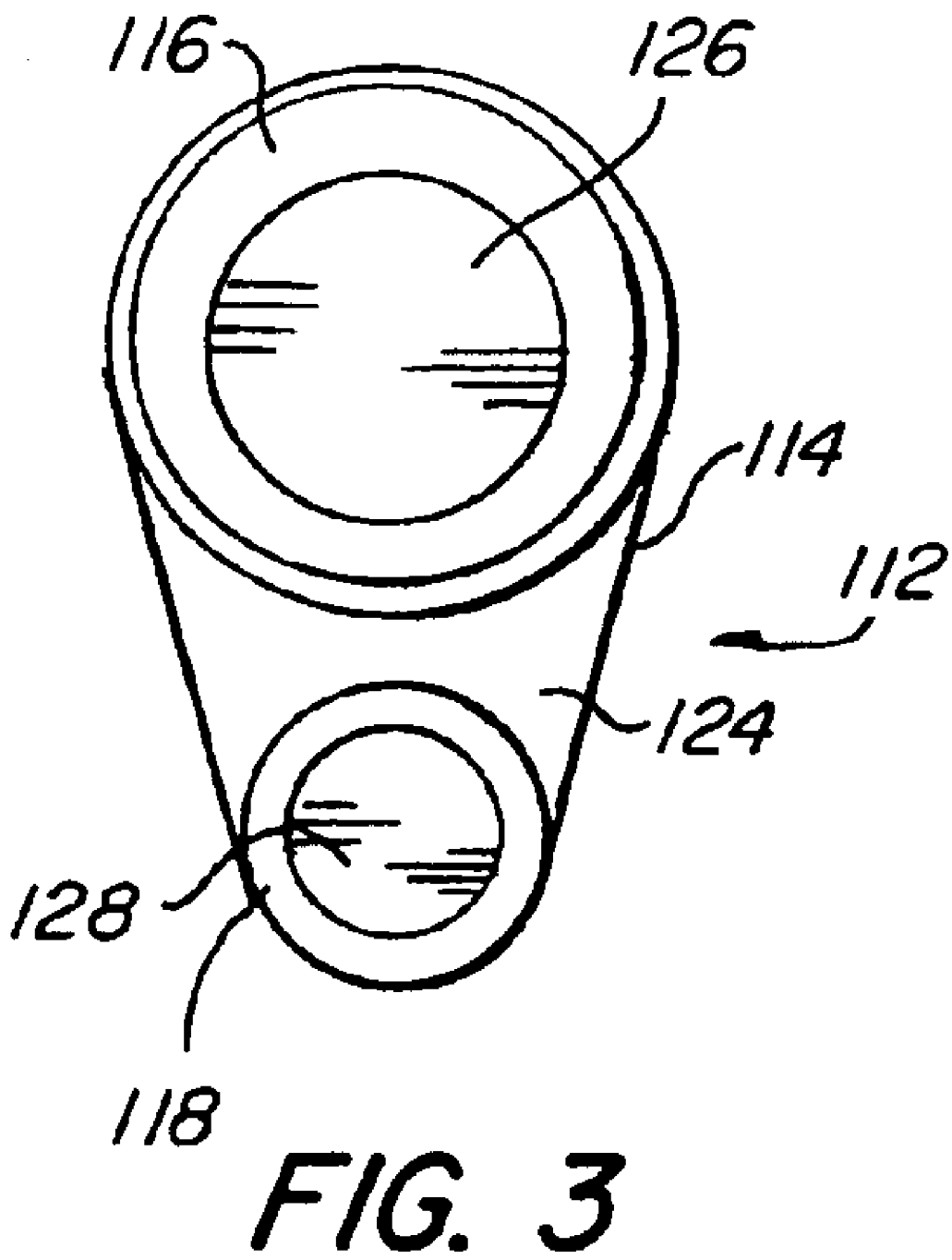
FIG. 3 is a cross-sectional view of the coupling element according to FIG. 1, showing the light and image guiding stems.

Referring now to FIG. 3, a cross-sectional view of coupling element 112 is illustrated. An approximately cylindrical image guiding stem 116 protrudes at one coupling end 124 of coupling element housing 114. The length and inside diameter of image guiding receptacle 108 are selected so that image guiding stem 116 can be received snugly therein. A window 126 is provided at the end of the image guiding stem 116 to provide a seal for the image guiding cable 104. An approximately cylindrical light guiding stem 118 extends from one coupling end 124 of coupling element housing 114 parallel to image guiding stem 116. The light guiding stem 118 is smaller in diameter and length than the image guiding stem 116. Also window 128 is provided at the end of the light guiding stem 118 to provide a seal for the light guiding cable 106.

Referring to FIGS. 1 and 2, image guiding stem 116 comprises a cylindrical segment 130, and annular groove 132, and a terminal conical segment 134. Both image guiding stem 116 and light guiding stem 118 extend in a coupling direction to mate with image guiding receptacle 108 and light guiding receptacle 110 respectively.

A locking element 136, displaceable radially with respect to the coupling direction, is located in housing 102. Locking element 136 may be approximately the shape of a two-tined fork that is bent inward in a circular shape at the outer end, the radius of curvature corresponding approximately to the radius of curvature of image guiding receptacle 108. The outer ends of locking element 136 project slightly into image guiding receptacle 108 as shown in FIG. 2.

Conical segment 134 of image guiding stem 116 thereby encounters the ends of locking element 136 projecting into image guiding receptacle 108 and displaces them radially outward.

When image guiding stem 116 has been pushed into image guiding receptacle 108 to the point that the ends of locking element 136 come to rest at the level of annular groove 132, they snap into annular groove 132.

In this position the coupling mechanism is now closed, i.e. camera unit 100 is coupled and mechanically interlocked to coupling element 112. In this state, window 126 of image guiding stem 116 and window 138 in the base of image guiding receptacle 108 lie congruently with one another, thus creating an image-guiding coupling. Window 128 of light guiding stem 118 comes to rest in front of window 140 of light guiding receptacle 110, so that a light-guiding coupling is also created.

All that is necessary to release the coupling is withdraw the coupling element 112 outward with enough force to overcome the locking element 136 as engaged in annular groove 132.

Figure 4A:
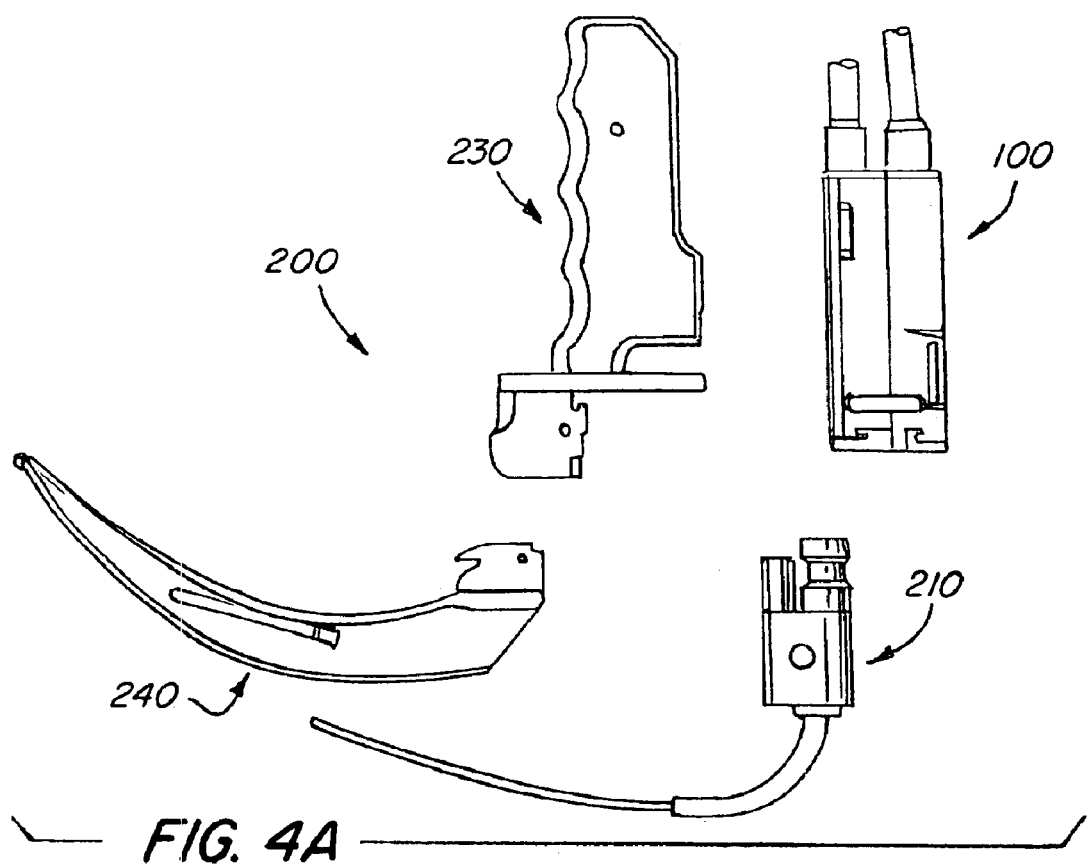
FIG. 4A is an illustration of a disassembled video laryngoscope system with, an interchangeable blade, a handle, a light and image guiding attachment, and a camera unit according to FIG. 1.
Figure 4B:
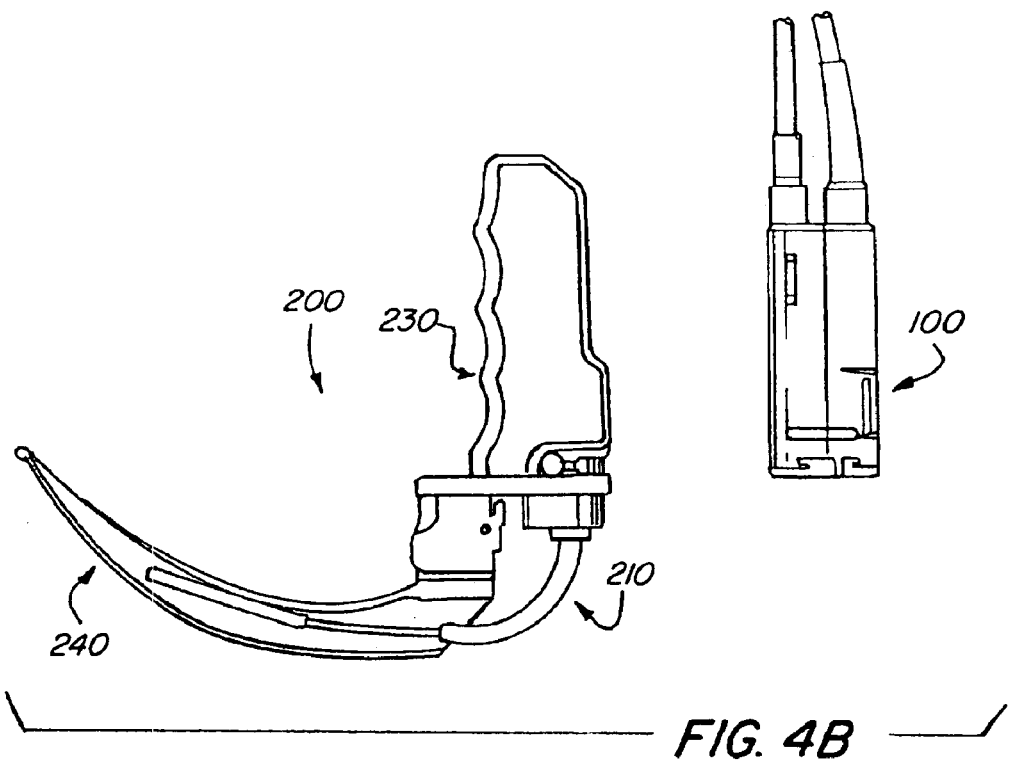
FIG. 4B is an illustration of a partially assembled video laryngoscope system with, an interchangeable blade and a light and image guiding attachment affixed to a handle, and a detached camera unit according to FIG. 1.
Figure 4C:
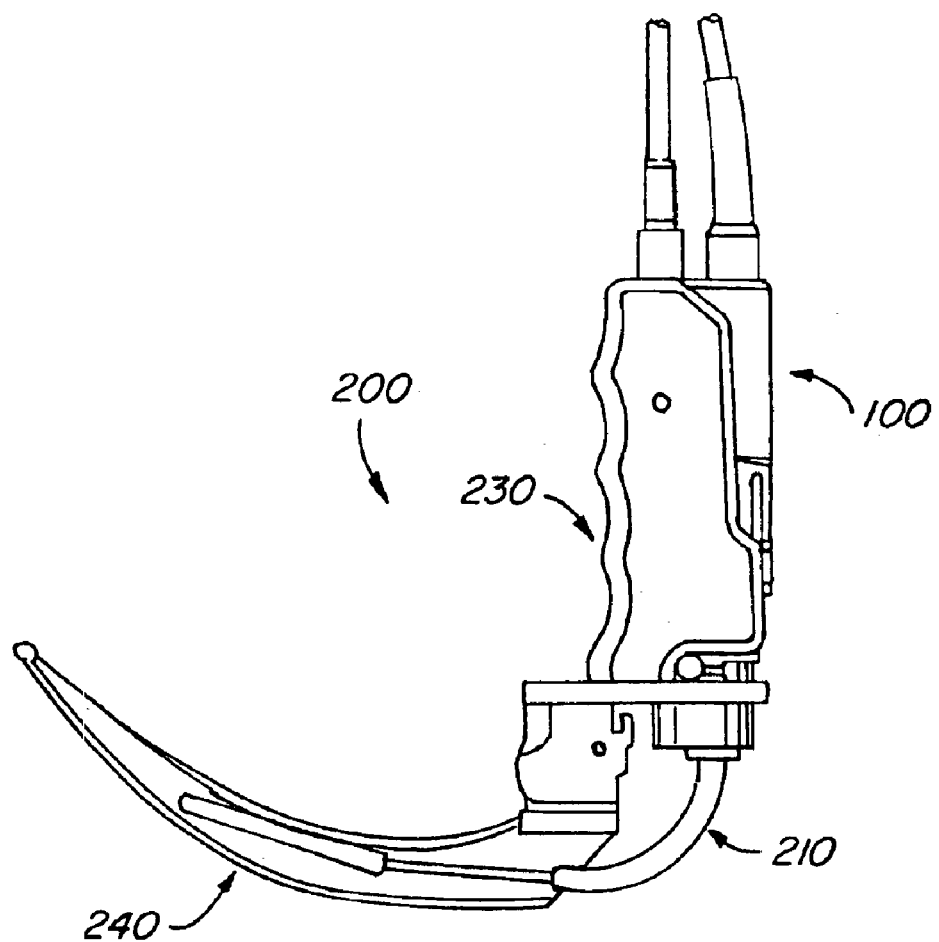
FIG. 4C is an illustration of a fully assembled video laryngoscope system with, an interchangeable blade, a light and image guiding attachment, and a camera unit affixed to a handle in an engaged position according to FIG. 1.

A video laryngoscope system 200 is illustrated in FIG. 4A. The video laryngoscope system 200 in FIG. 4A is shown disassembled and comprises four basic parts. These basic parts include camera unit 100, light and image guiding attachment 210, handle 230, and blade 240. The assembly of these four basic parts is progressively illustrated in FIGS. 4A–4C. FIGS. 4A–4C will now be discussed in conjunction with FIGS. 5, 6 and 7.

Figure 5:
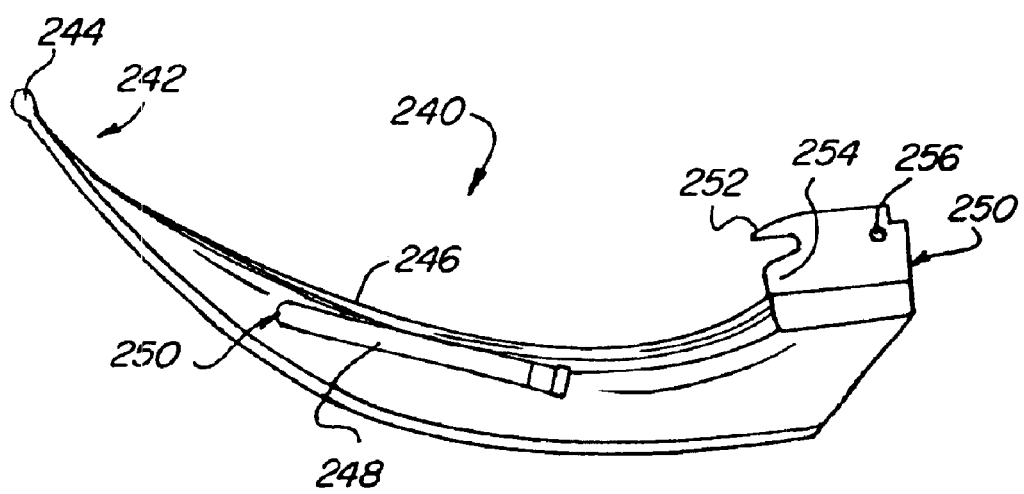
FIG. 5 is an illustration of the detached interchangeable blade according to FIGS. 4A–4C.

In FIG. 4B is illustrated the attachment of blade 240 to handle 230. As can be seen in FIG. 5, the shape of blade 240 is curved in this illustration; however, a straight blade may also be utilized as desired. Blade 240 has a distal end 242 which may be smoothed by a bulb-like edge 244. Blade 240 also has a curved top surface 246 that may be used to elevate the tongue and permit the visualization of the vocal cords beneath it. Also illustrated in FIG. 5 is sheath 248, which is designed to receive the distal end of light and image guiding attachment 210 so and to provide additional support to rigidly hold it in position and align the distal end of the light and image guiding attachment 210 with the distal end of blade 240. Sheath 248 also may alternatively be provided with a window 250 located at a distal end of sheath 248, which acts as a seal for sheath 248. Blade 240 is provided such that it may be easily and quickly interchanged with another as desired. This provides increased versatility for the physician where the blade 240 may be individually selected according to the needs of the patient.

Figure 6:
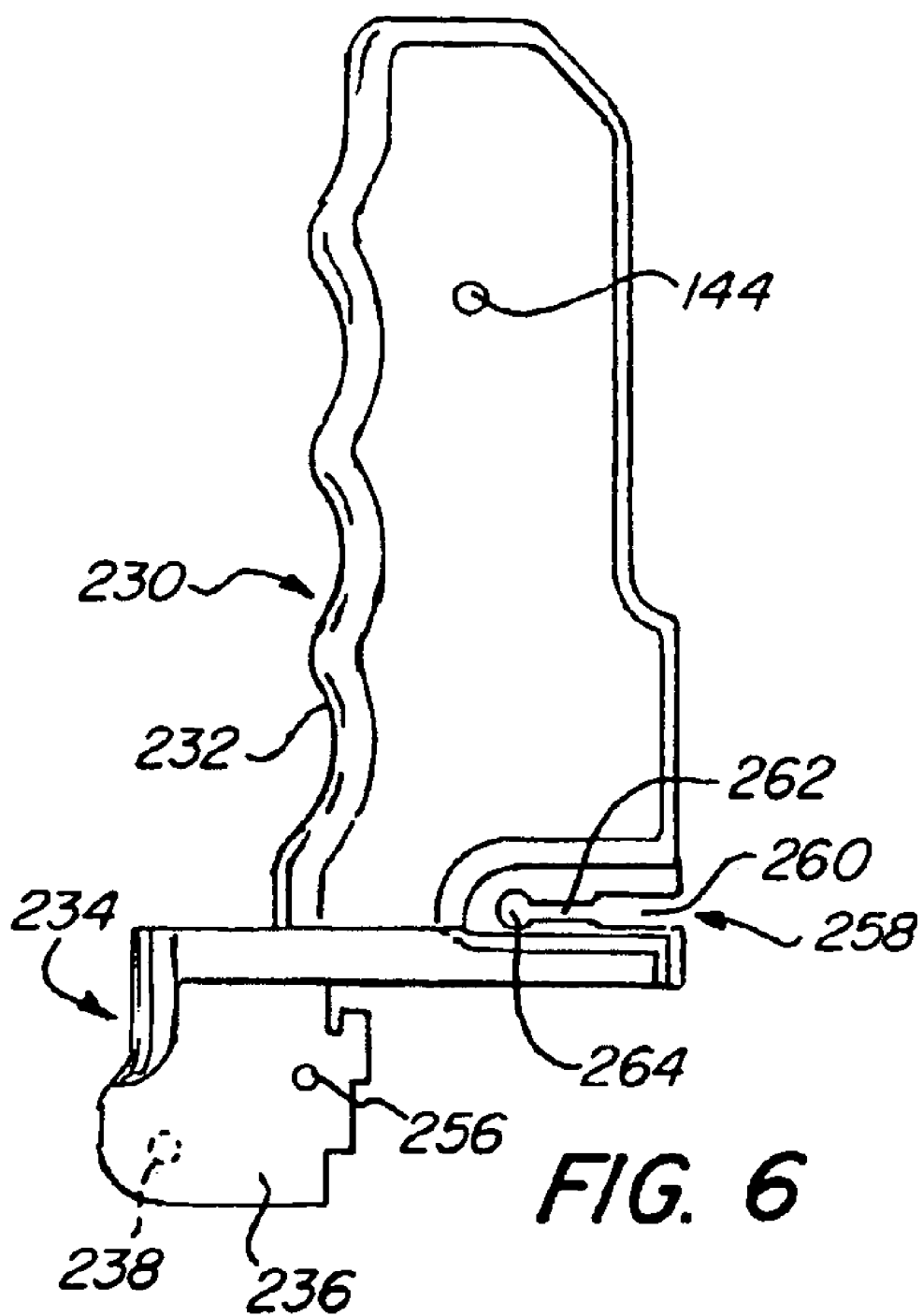
FIG. 6 is an illustration of the handle according to FIGS. 4A–4C.

Referring to FIG. 6, handle 230 is illustrated and is typically cylindrical with a formed outer surface 232 thereby facilitating a secure gripping surface. As can be seen in FIG. 4B, handle 230 is detachably joined to a blade 240 by a hinge-type joiner 234 such that any number of varying blades 240 may be interchanged for use with handle 230.

The hinge-type joiner 234 includes a conventional hinge socket 236 and connector 250 (FIG. 5) respectively mounted to the lower end of the handle 230 and to the blade 240 respectively. Hinge socket 236 further includes a crossbar 238. Connector 250 includes a hook 252 in a block 254 that fits into hinge socket 236. Hook 252 engages the crossbar 238, and the handle 230 is rotated 90 degrees so that blade 240 will be rigidly held to handle 230. This is a common hinge-type joinder 234 used in this type of instrumentation and is useful for all blade forms, of which the illustrated form is merely an example. A ball detent 256 detachably retains the handle 230 and blade 240 together and erect in the assembled configuration. The assembled instrument is rigid during the procedure.

Further provided on handle 230 is slot 258, which is provided with an outer section 260, a restriction 262, and seat 264. Slot 258 is designed to engage with light and image guiding attachment 210, which will be discussed in connection with FIG. 4B.

Figure 7:
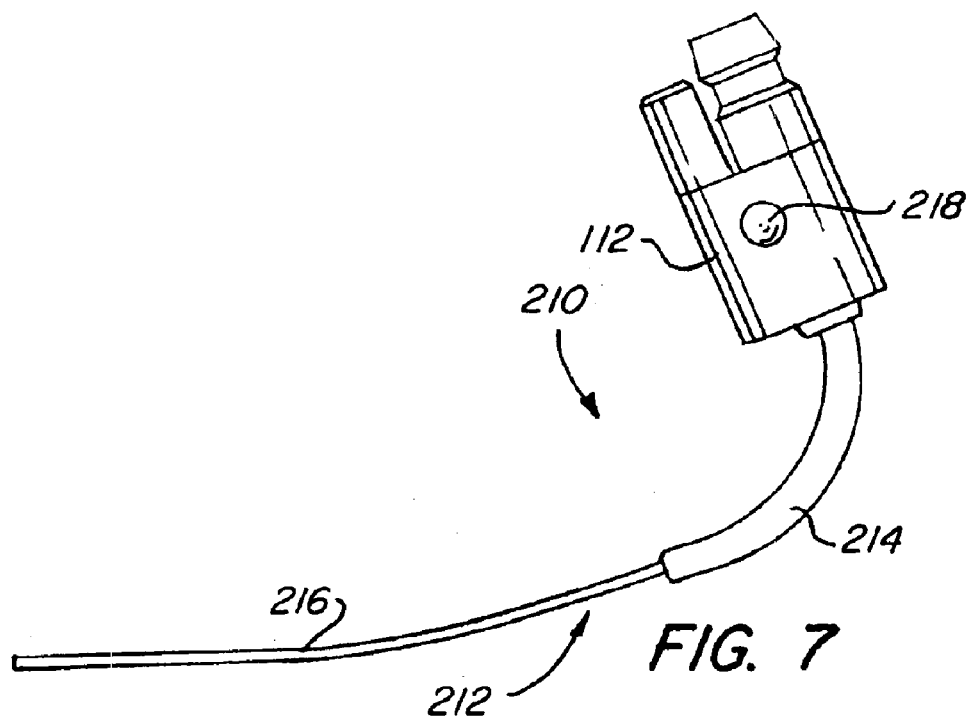
FIG. 7 is an illustration of the detached light and image guiding attachment with the coupling element according to FIGS. 4A–4C.

Also illustrated in FIG. 4B is the engagement of light and image guiding attachment 210 with both blade 240 and handle 230. As illustrated in FIG. 7, light and image guiding attachment 210 incorporates coupling element 112. In addition, light and image guiding attachment 210 includes an elongated shaft 212 that includes a curved portion 214 connected to coupling element 112 and an extended shaft 216. The extended shaft is shown slightly curved but may be made in any shape desired. Elongated shaft 212 comprises a rigid material, typically stainless steel, so as to hold its shape, but may be manufactured on any rigid non-corroding material. Elongated shaft 212 contains both the light and image guiding systems. The light guiding system is provided for transmitting illuminating light ahead of blade 240, while the image guiding system is provided for receiving reflected light and transmitting it back to camera unit 100. Also provided at the distal end of light and image guiding attachment 210 is a window 220, which acts as a seal protecting both the light and image guiding systems contained in light and image guiding attachment 210. The rigid construction of elongated shaft 212 provides further protection against, for instance, bending or kinking of the light and image guiding systems.

Protrusion 218 is further provided on light and image guiding attachment 210, which is located on either side of coupling element 112. Light and image guiding attachment 210 may easily be engaged with both blade 240 and handle 230 as the following description will illustrate. The distal end of elongated shaft 212 is designed to engage with sheath 248 on blade 240. As seen in FIG. 4B, the distal end of elongated shaft 212 is slid into sheath 248, which will keep elongated shaft 212 rigidly aligned with blade 240. As can also be seen from FIG. 4B, protrusion 218 coacts with slot 258 to engagingly slide past restriction 262 and into seat 264. At this point, blade 240 and light and image guiding attachment 210 are both engaged with handle 230.

Referring to FIG. 4C, camera unit 100 is shown affixed to light and image guiding attachment 210 and handle 230. Camera unit 100 may easily be engagingly attached to light and image guiding attachment 210 as previously described in connection with FIGS. 1–3 and will not be re-described here.

Also provided on camera unit 100 is a recess 140, which engages with a locking mechanism 144, provided in handle 230. Locking mechanism can comprise any appropriate mechanical interlocking system that may be engaged by insertion of camera unit 100 into handle 230, such as for instance, a ball detent or equivalent engagement means.

As illustrated in FIG. 4C, video laryngoscope system 200 may quickly and easily be assembled and disassembled by a physician without the need to see the device. Rather, the physician, based upon the construction and keying of the four main parts, may assemble and disassemble the video laryngoscope system 200 simply by feel of the parts. In addition, the rugged construction of the parts will provide for greater lifespan of the equipment.

Image guiding cable 104 connected to camera unit 100 may be attached to a video screen (not shown) to be viewed by the physician using the video laryngoscope 200. Image guiding cable 104 may be directly connected to a video screen (not shown) or may attach to other electronic control circuitry, depending upon the selected format and application.

Instead of the camera and illumination arrangements already described, there are other alternatives, which can be used in any combination. For example, instead of employing a separate light source (not shown), a portable power and light source may be located in handle 230. This, for instance, would eliminate the need for light guiding cable 106 and the need for a separate light source.

Figure 8A:
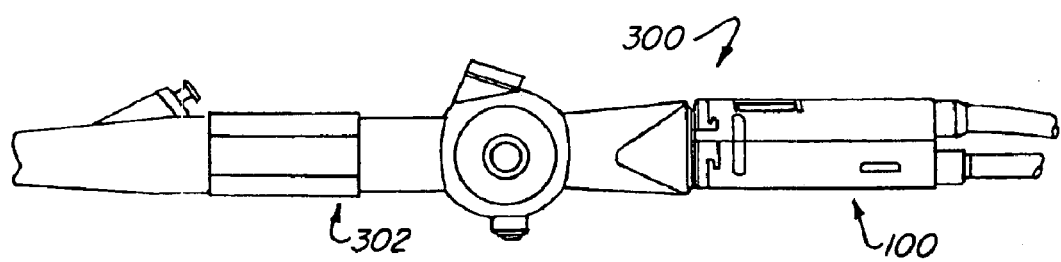
FIG. 8A is an illustration of a disassembled endoscope system with an endoscope, and a camera unit according to FIG. 1.
Figure 8B:
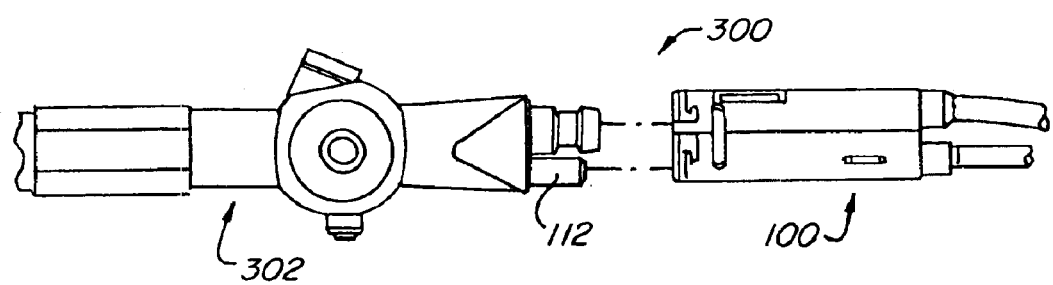
FIG. 8B is an illustration of a fully assembled endoscope system with the endoscope in an engaged position with the camera unit according to FIG. 1.

Referring now to FIGS. 8A and 8B, an endoscope system 300 is illustrated. In FIG. 8A endoscope system 300 is shown disassembled with camera unit 100 detached from endoscope 302. Endoscope 302 comprises coupling element 112, which is lockingly engagable with camera unit 100 as previously discussed in connection with FIGS. 1–3 and will not be re-described here. Endoscope 302 may comprise any type of endoscope desired for the particular procedure, for instance, having a rigid shaft, a semi-rigid shaft, or a flexible/articulating shaft. Coupling element 112 coacts with light and image guiding systems located in endoscope 302 to transmit illuminating light, from a light source (not shown) to an area ahead of endoscope 302, and to transmit reflected light back from the area ahead of endoscope 302 to camera 100 for translation into an electronic format.

FIG. 8B illustrates endoscope system 300 in an attached position, where endoscope 302 is lockingly engaged with camera unit 100 in a manner previously described in connection with FIGS. 1–3.

Many of the advantages discussed in connection with the video laryngoscope system 200 are realized with the endoscope system 300 that utilizes the same coupling mechanism. For instance, attachment and detachment of endoscope 302 with camera unit 100 is quick and easy. Keying of coupling element 112 and image guiding receptacle 108 and light guiding receptacle 110 will prevent inverted attachment of the two devices. As a result, the physician need only feel endoscope 302 and camera unit 100 in order to attach them.

Although the invention has been described with reference to a particular arrangement of parts, features and the like, for instance a video laryngoscope system and an endoscope system, these are not intended to exhaust all possible arrangements or features, and indeed many other modifications and variations will be ascertainable to those of skill in the art.

What is claimed is:

1. A coupling mechanism for a light and image guiding system comprising:
    a camera with a housing having an image guiding receptacle and a light guiding receptacle;
    a coupling element detachably engagable with said camera along a direction of movement, said coupling element having:
        an image guiding stem, for an image guiding system, that is engagable along the direction of movement with the image guiding receptacle; and
        a light guiding stem, for a light guiding system, that is engagable along the direction of movement with the light guiding receptacle; and
    an interlock configured as a locking element that is displaceable transversely to the direction of movement where said camera detachably interlocks with said coupling element when in an engaged position, the locking element comprising a recess.

2. The coupling mechanism according to claim 1 further comprising a light source, said light source connected to said camera unit by a light guiding cable.

3. The coupling mechanism according to claim 1 further comprising a video display, said video display connected to said camera unit by an image guiding cable.

4. The coupling mechanism according to claim 1 wherein said image guiding stem has a greater diameter than said light guiding stem such that said image guiding stem may not be inserted into said light guiding receptacle.

5. The coupling mechanism according to claim 1 wherein the coupling element is attached to an image and light guiding attachment device for use with a video laryngoscope.

6. The coupling mechanism according to claim 1 wherein the coupling element is attached to an endoscope.

7. The coupling mechanism according to claim 6 wherein an endoscope-specific coding element that is coupled to a read element on said camera upon attachment, is provided on said endoscope.

8. A light and image guiding coupling mechanism for a camera comprising:
    a first image guiding system having a first coupling engagable along a direction of movement with a first coupling of a second image guiding system, said first image guiding system communicating with the second image guiding system when said first coupling is engaged with the second coupling;
    a first light guiding system having a first coupling engagable along a direction of movement with a first coupling of a second light guiding system, said first light guiding system communicating with the second light guiding system when said first coupling is engaged with the second coupling; and
    an interlock system configured as a locking element with a recess, the locking element displaceable transversely to the direction of movement, said first image guiding system and said first light guiding system interlocking with the second image guiding system and the second light guiding system respectively when in an engaged position.

9. The coupling mechanism according to claim 8 further comprising a light source, said light source connected to said camera unit by a light guiding cable.

10. The coupling mechanism according to claim 8 further comprising a video display, said video display connected to said camera unit by an image guiding cable.

11. The coupling mechanism according to claim 8 wherein the first light guiding system and the second light guiding system are located in an image and light guiding attachment device for use with a video laryngoscope.

12. The coupling mechanism according to claim 8 wherein the first light guiding system and the second light guiding system are located in an endoscope.

13. A video laryngoscope coupling mechanism comprising:
    a handle;
    a blade detachably connectable to said handle;
    a camera detachably connectable to said handle and having a housing with an image guiding receptacle and a light guiding receptacle;
    a light and image guiding attachment detachably connectable to said handle and having a coupling element detachably engagable along a direction of movement with said camera, said coupling element having:
  an image guiding stem, for an image guiding system, that is engagable along the direction of movement with said image guiding receptacle; and
  a light guiding stem, for a light guiding system, that is engagable along the direction of movement with said light guiding receptacle.

14. The coupling mechanism according to claim 13 further comprising an interlock configured as a locking element that is displaceable transversely to the direction of movement where said camera unit detachably interlocks with said coupling element when in an engaged position, the locking element comprising a recess.

15. The coupling mechanism according to claim 13 further comprising a light source, said light source connected to said camera unit by a light guiding cable.

16. The coupling mechanism according to claim 13 further comprising a video display, said video display connected to said camera unit by an image guiding cable.

17. The coupling mechanism according to claim 13 wherein said light and image guiding attachment is rigid.

18. The coupling mechanism according to claim 17 wherein said light and image guiding attachment comprises stainless steel.

19. The coupling mechanism according to claim 13 wherein said handle has a slot cut therein for pivotally receiving said light and image guiding attachment.

20. The coupling mechanism according to claim 19 wherein said light and image guiding attachment has a protrusion extending therefrom to engage with said slot located in said handle.

21. The coupling mechanism according to claim 13 wherein said handle has a cavity provided therein for engagably receiving said camera unit.

22. The coupling mechanism according to claim 13 wherein said blade has a recess provided therein for receiving a distal end of said light and image guiding attachment.

23. An endoscope coupling mechanism comprising:
  a camera having a housing with an image guiding receptacle and a light guiding receptacle;
  an endoscope having a coupling element detachably engagable along a direction of movement with said camera, said coupling element having:
    an image guiding stem, for an image guiding system, that is engagable along the direction of movement with said image guiding receptacle; and
    a light guiding stem, for a light guiding system, that is engagable along the direction of movement with said light guiding receptacle.

24. The coupling mechanism according to claim 22 further comprising an interlock configured as a locking element that is displaceable transversely to the direction of movement where said camera unit detachably interlocks with said coupling element when in an engaged position, the locking element comprising a recess.

25. The coupling mechanism according to claim 23 further comprising a light source, said light source connected to said camera unit by a light guiding cable.

26. The coupling mechanism according to claim 23 further comprising a video display, said video display connected to said camera unit by an image guiding cable.

27. An endoscope coupling mechanism comprising:
  an image guiding stem for an image guiding system, said image guiding stem forming an image guiding coupling for connecting along a direction of movement to a camera;
  a light guiding stem for a light guiding system, said light guiding stem forming a light guiding coupling for connecting along the direction of movement to a camera; and
  an interlock system configured as a locking element, displaceable transversely to the direction of movement, the camera detachably interlocking with said endoscope when in an engaged position, the locking element further comprising a recess.

* * * * *

UNITED STATES PATENT AND TRADEMARK OFFICE
CERTIFICATE OF CORRECTION

PATENT NO. : 6,875,169 B2
DATED : April 5, 2005
INVENTOR(S) : George Berci et al.

It is certified that error appears in the above-identified patent and that said Letters Patent is hereby corrected as shown below:

Title page,
Item [75], Inventors, should read:
-- [75] Inventors: George Berci, Los Angeles, CA (US);
Marshal B. Kaplan, Beverly Hills, CA (US); James P. Barry, Charlton, MA (US); David Chatenever, Santa Barbara, CA (US); Klaus M. Irion, Liptingen (DE); Andre Ehrhardt, Wurmlingen (DE); Jurgen Rudischhauser, Tuttlingen (DE); Daniel Mattsson-Boze, Sacramento, CA (US) --

Signed and Sealed this

Thirty-first Day of May, 2005

JON W. DUDAS
*Director of the United States Patent and Trademark Office*